US011043302B2

(12) United States Patent
Muuranto et al.

(10) Patent No.: US 11,043,302 B2
(45) Date of Patent: *Jun. 22, 2021

(54) COMMON DISPLAY UNIT FOR A PLURALITY OF CABLELESS MEDICAL SENSORS

(71) Applicant: General Electric Company, Schenectady, NY (US)

(72) Inventors: Erno Petteri Muuranto, Helsinki (FI); Magnus Kall, Helsinki (FI); Emma Elina Ikonen, Helsinki (FI); Kristian Matti Karru, Helsinki (FI); Otto Valtteri Pekander, Helsinki (FI); Ville Petteri Vartiovaara, Helsinki (FI); Henrik Ekman, Helsinki (FI)

(73) Assignee: General Electric Company, Schenectady, NY (US)

( * ) Notice: Subject to any disclaimer, the term of this patent is extended or adjusted under 35 U.S.C. 154(b) by 9 days.

This patent is subject to a terminal disclaimer.

(21) Appl. No.: 16/238,350

(22) Filed: Jan. 2, 2019

(65) Prior Publication Data

US 2019/0133484 A1 May 9, 2019

Related U.S. Application Data

(63) Continuation of application No. 14/586,393, filed on Dec. 30, 2014, now Pat. No. 10,881,314.

(51) Int. Cl.
*G16H 40/67* (2018.01)
*A61B 5/0205* (2006.01)
(Continued)

(52) U.S. Cl.
CPC ............ *G16H 40/67* (2018.01); *A61B 5/0022* (2013.01); *A61B 5/0024* (2013.01);
(Continued)

(58) Field of Classification Search
CPC . A61B 5/0022; A61B 5/0024; A61B 5/02055; A61B 5/022; A61B 5/02416;
(Continued)

(56) References Cited

U.S. PATENT DOCUMENTS 8,704,666 B2 * 4/2014 Baker, Jr. ............ A61B 5/14551
340/573.1
2004/0130446 A1 7/2004 Chen
(Continued)

OTHER PUBLICATIONS

International Search Report and Written Opinion for PCT/US2015/050698, dated Dec. 9, 2015, 15 pages.

*Primary Examiner* — Lynsey C Eiseman
*Assistant Examiner* — Amanda L Steinberg
(74) *Attorney, Agent, or Firm* — Andrus Intellectual Property Law, LLP

(57) ABSTRACT

A wireless patient monitor comprises a generic activator module having a universal connection port that connects with any one of multiple sensor devices, a battery, and a radio transmitter wirelessly connected to a host device. The generic activator module connects to any one of multiple sensor devices via the universal connection port to provide power from the battery to the sensor device and to receive digital physiological data from the sensor device. The radio transmitter transmits the digital physiological data received from the sensor device to a host device.

19 Claims, 6 Drawing Sheets

(51) Int. Cl.
*A61B 5/1455* (2006.01)
*A61B 5/00* (2006.01)
*A61B 5/304* (2021.01)
*A61B 5/339* (2021.01)
*A61B 5/369* (2021.01)
*A61B 5/01* (2006.01)
*A61B 5/022* (2006.01)
*A61B 5/024* (2006.01)
*A61B 5/318* (2021.01)

(52) U.S. Cl.
CPC ...... *A61B 5/02055* (2013.01); *A61B 5/14552* (2013.01); *A61B 5/304* (2021.01); *A61B 5/339* (2021.01); *A61B 5/369* (2021.01); *A61B 5/4821* (2013.01); *A61B 5/0006* (2013.01); *A61B 5/0008* (2013.01); *A61B 5/01* (2013.01); *A61B 5/022* (2013.01); *A61B 5/02416* (2013.01); *A61B 5/02438* (2013.01); *A61B 5/318* (2021.01); *A61B 2560/0214* (2013.01); *A61B 2560/045* (2013.01); *A61B 2562/222* (2013.01); *A61B 2562/227* (2013.01)

(58) Field of Classification Search
CPC . A61B 5/02438; A61B 5/04288; A61B 5/044; A61B 5/0476; A61B 5/045; A61B 5/0402; A61B 5/14552; A61B 5/4821; A61B 5/222; G06F 19/3418
See application file for complete search history.

(56) References Cited

U.S. PATENT DOCUMENTS

| | | |
|---|---|---|
| 2004/0199056 A1 | 10/2004 | Russ |
| 2006/0122466 A1 | 6/2006 | Nguyen-Dobinsky et al. |
| 2006/0155589 A1* | 7/2006 | Lane .................... A61B 5/0002 705/4 |
| 2006/0282021 A1 | 12/2006 | DeVaul |
| 2007/0027367 A1 | 2/2007 | Oliver |
| 2007/0123783 A1 | 5/2007 | Chang |
| 2007/0179734 A1 | 8/2007 | Chmiel et al. |
| 2008/0215360 A1 | 9/2008 | Dicks et al. |
| 2008/0281168 A1 | 11/2008 | Gibson et al. |
| 2009/0312638 A1 | 12/2009 | Bartlett |
| 2010/0249540 A1 | 9/2010 | Lisogurski |
| 2011/0021930 A1 | 1/2011 | Mazzeo et al. |
| 2015/0160048 A1* | 6/2015 | Schuessler ............. G04G 17/04 73/866.5 |

* cited by examiner

COMMON DISPLAY UNIT FOR A PLURALITY OF CABLELESS MEDICAL SENSORS

FIELD

This application is a continuation of U.S. patent application Ser. No. 14/586,393, filed Dec. 30, 2014, which is incorporated herein by reference in entirety.

BACKGROUND

The present disclosure relates generally to medical devices and, more specifically, to medical monitoring devices for monitoring a patient's physiology and health status.

In the field of medicine, physicians often desire to monitor multiple physiological characteristics of their patients. Oftentimes, patient monitoring involves the use of several separate monitoring devices simultaneously, such as a pulse oximeter, a blood pressure monitor, a heart monitor, a temperature monitor, etc. Several separate patient monitoring devices are often connected to a patient, tethering the patient to multiple bulky bedside devices via physical wiring or cables. Multi-parameter monitors are also available where different sensor sets may be connected to a single monitor. However, such multi-parameter systems may be even more restrictive than separate monitoring devices because they require all of the sensors attached to a patient to be physically attached to the monitor, resulting in multiple wires running across the patient's body. Thus, currently available patient monitoring devices often inhibit patient movement, requiring a patient to stay in one location or to transport a large monitor with them when they move from one place to another. Further, currently available monitoring devices are often power intensive and either require being plugged in to a wall outlet or require replacing and recharging the device battery every few hours.

SUMMARY

One embodiment of a wireless patient monitor comprises a generic activator module having a universal connection port that connects with any one of multiple sensor devices, a battery, and a radio transmitter wirelessly connected to a host device. The generic activator module connects to any one of multiple sensor devices via the universal connection port to provide power from the battery to the sensor device and to receive digital physiological data from the sensor device. The radio transmitter transmits the digital physiological data received from the sensor device to a host device.

Another embodiment of a patient monitoring system comprises a first sensor device having a first set of one or more detectors to collect a first physiological information from a patient, a first analog-to-digital converter to convert the first physiological information to a first digital physiological data, and a first connector configured to transmit the first digital physiological data and to receive power to power the first sensor device. A second sensor device has a second set of one or more detectors to collect a second physiological information from the patient, a second analog-to-digital converter to convert the second physiological information to a second digital physiological data, and a second connector configured to transmit the second digital physiological data and to receive power to power the second sensor device. The system further includes a generic activator module capable of alternately connecting with the first sensor device and the second sensor device. The generic activator has a battery, a universal connection port configured to connect with the first connector and the second connector to provide power from the battery to the first sensor device and the second sensor device and to receive digital physiological data from the first sensor device and the second sensor device, and a radio transmitter configured to transmit the first digital physiological data and the second digital physiological data to a host device.

Another embodiment of a patient monitoring system comprises a sensor device having one or more detectors to collect physiological information from a patient, an analog-to-digital converter to convert the physiological information to a digital physiological data, and a connector configured to transmit the digital physiological data and receive power to power the sensor device. The sensor device may be any one of multiple types of sensor devices. The patient monitoring system further includes a generic activator module having a battery, a universal connection port configured to connect with the connector to provide power from the battery to the sensor device and to receive digital physiological data from the sensor device, and a radio transmitter to transmit the digital physiological data. The generic activator module also has a display that displays a charge status of the battery and a connection status between the radio transmitter and a host device. The system further includes a host device to receive the digital physiological data from the radio transmitter.

BRIEF DESCRIPTION OF THE DRAWINGS

The drawings illustrate the best mode presently contemplated of carrying out the disclosure. In the drawings.

DETAILED DESCRIPTION OF THE INVENTION

Figure 1:
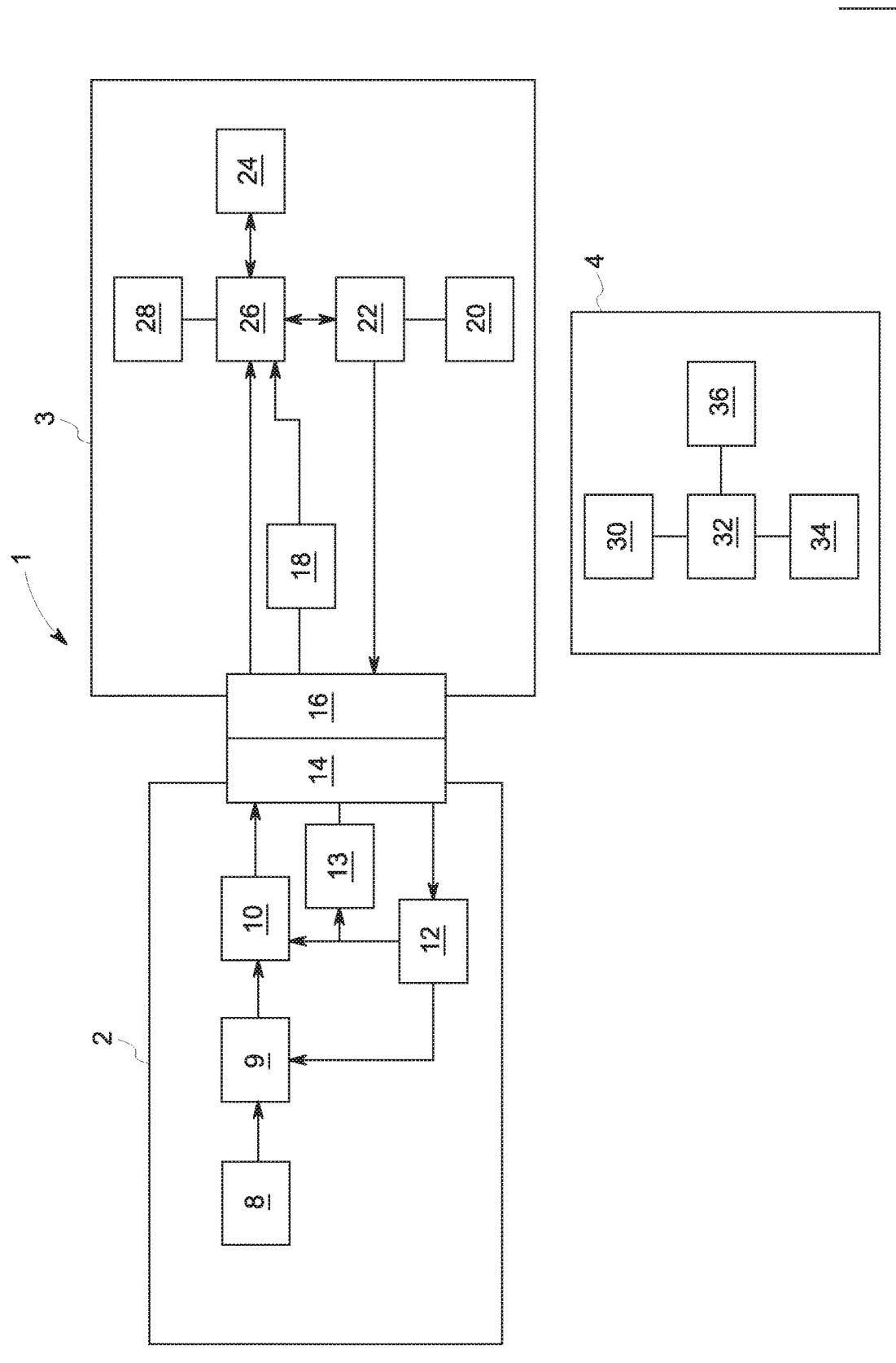
FIG. 1 is a block diagram of one embodiment of a wireless patient monitoring system including a sensor device, a generic activator device, and a host device.
Figure 2:
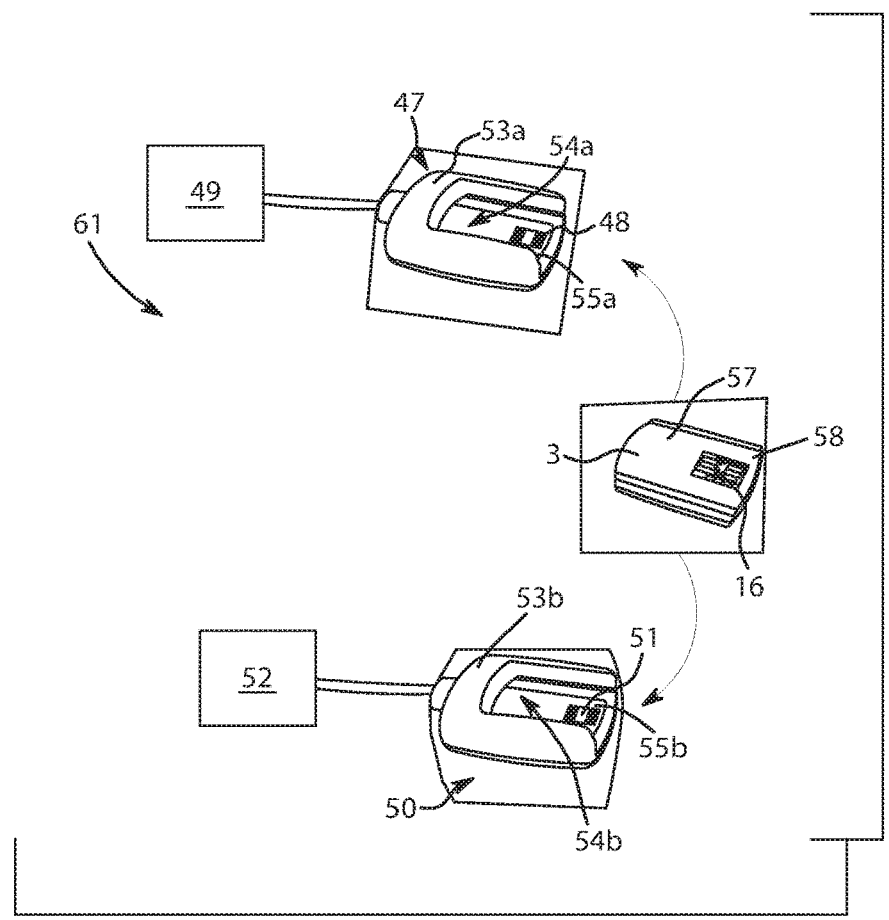
FIG. 2 depicts one embodiment of a wireless patient monitor including a first sensor device, a second sensor device, and a generic activator module.

FIG. 1 depicts one embodiment of a wireless patient monitoring system 1 including a sensor device 2, a generic actuator module 3 and a host device 4. FIG. 2 depicts one embodiment of a wireless patient monitoring system demonstrating the interaction between one or more sensor devices and the generic actuator module 3. The generic activator module 3 is connectable with any one of several different types of sensor devices 2 to provide power to the sensor device 2 and to transmit the digital physiological data produced by the sensor device 2 to a host device 4. A monitoring system, such as that shown in FIG. 2, may further include any number of generic activator modules 3 that are interchangeable with one another and are each configured to pair with any of the available types of sensor devices. The generic activator modules 3 may be rechargeable, such as by containing rechargeable batteries, and may be interchanged in order to maintain power to any sensor device 2.

For example, the generic actuator module 3 demonstrated in FIG. 2 is connectable to any one of a number of different sensor devices 2 such as the first sensor device 47 and the second sensor device 50. The first sensor device 47 has a first set of patient sensors 49, and the second sensor device 50 has a second set of patient sensors 52. The first sensor device 47 and the second sensor device 50 may be any devices for sensing patient physiological data. For example, the first sensor device 47 may be an ECG sensor device wherein the first patient sensors 49 are ECG leads, and the second sensor device 50 may be an EEG sensor device wherein the second patient sensors 52 are EEG leads. The generic activator module 3 of FIG. 2 may be inserted into or otherwise connected with either of the first sensor device 47 or the second sensor device 50 to activate that device 47 or 50 and transmit the data collected by that device to the host device. Such connection is made by positioning generic activator module 3 so that the universal connection port 16 of the generic activator module 3 is in contact with the connector 48 of the first sensor device 47 or the connector 51 of the second sensor device 50. In FIG. 2, the first sensor device 47 has a first sensor device housing 53a and the second sensor device 50 has a second sensor device housing 53b. The activator module 3 is contained in an activator module housing 57. The first sensor device housing 53a and the second sensor device housing 53b are each shaped to pair with the activator module housing 57, and vice versa. Each of the first sensor device housing 53a and the second sensor device housing 53b have a connection portion 54a, 54b, which are identically shaped to slidably connect with the activator module housing 57, where the activator module slides onto a respective one of the sensor device housings 53a, 53b at the connection portion 54a, 54b. Each connection portion 54a, 54b has a respective front face 55a, 55b and the connector is positioned on the front face 55a, 55b. The activator module housing 57 has a back face 58. When the activator module housing 57 slidably connects with the first sensor device housing 53a or the second sensor device housing 53b, the back face 58 of the activator module housing 57 slides against the front face 55a, 55b of the respective sensor device housing 53a, 53b. The universal connection port 16 contacts the respective one of the first connector 48 and the second connector 51 once the activator module housing 57 is fully slidably connected to the paired sensor device housing 53a, 53b. It should be understood that contact between the generic activator module 3 and the first or second sensor devices 47, 50 may be an electrical contact or any other connection that allows communication and power transfer. In alternative embodiments, the connection may be through means not requiring galvanic contact between the generic activator module 3 and the first or second sensor devices 47, 50. For example, the generic activator module 3 may be connected to the first or second sensor devices 47, 50 via an optical data transfer and a capacitive power transfer. Additionally, the generic activator module 3 may be configured to process the physiological data from the various sensor devices, such as the EEG data or ECG data in the present example, and/or to display physiological information about the patient derived from the physiological data.

Returning to FIG. 1, the depicted embodiment has a sensor device 2 with one or more patient sensors or detectors 8 connected to a processor 10. The one or more patient detectors 8 may include any sensors, leads, or other devices available in the art for sensing or detecting physiological information from a patient, which may include but are not limited to electrodes, lead wires, or available physiological measurement devices such as blood pressure cuffs, pulse oximetry sensors, temperature sensors, etc. The physiological signals recorded by the patient detectors 8 are digitized by analog-to-digital converter (A/D converter) 9. The A/D converter 9 may be any device or logic set capable of digitizing analog physiological signals. For example, the A/D converter 9 may be an Analog Front End (AFE). Processor 10 receives the digital physiological data from the A/D converter 9 and may transmit the processed data and the raw digitized physiological data to the generic activator module 3 via the connector 14.

The processor 10 may be configured to perform various functions depending on the type of sensor device 2 detected. For example, if the sensor device 2 is a noninvasive blood pressure (NIBP) monitor then the processor may be configured to process the physiological data detected by the sensors in a blood pressure cuff to calculate systolic, diastolic and mean blood pressure values. Likewise, the processor 10 may also be configured to determine a heart rate when the generic activator module 3 is connected to an ECG sensor device. Likewise, the processor 10 may be configured to determine a blood oxygenation value for the patient when the generic activator module 3 is connected to a sensor device 2 that is a pulse oximeter sensor device. Likewise, the processor 10 may be configured to also detect when it is connected to an electroencephalograph (EEG) sensor device and then determine a depth of anesthesia measurement value, such as an entropy value or a sedation responsiveness index value. In an embodiment where the sensor device 2 is a thermometer or temperature sensor device, the processor 10 may be configured to determine a temperature for the patient, such as a mean temperature. Alternatively or additionally, the processor 26 of the generic activator module 3 may be configured to process the digital physiological data from the sensor device 2 to calculate any or all of those aforementioned values. It should be understood that the device and system of the present disclosure is not limited to the examples provided, but may be configured and employed to monitor any clinical parameter. The examples provided herein are for the purpose of demonstrating the invention and should not be considered limiting.

In another alternative embodiment, the sensor device 2 may not contain any processor. In such an embodiment, the digitized physiological data would be sent from the A/D converter 9 of the sensor device 2 to the generic activator module 3. Accordingly, the generic activator module 3 may be configured to receive digitized raw data or digitized filtered data from various types of sensor devices 2, which is the physiological data detected by the patient detectors 8 of the various sensor devices that has been digitized by the A/D converter 9.

The processor 10 and the A/D converter 9 receive power from the power supply 12. The power supply 12 may be a simple conductor that conducts power received from the generic activator module 3 via the connector 14. Alternatively, the power supply 12 may include a battery that stores energy received from the generic activator module 3 and distributes that power to the various powered elements of the sensor device 2. Moreover, the power supply 12 may further include power management capabilities. This may be the case in embodiments where the sensor device 2 contains more demanding electromechanical aspects, such as a non-invasive blood pressure monitor. In other embodiments where the sensor device 2 has only simple components, such as an embodiment only having patient sensors 8 and an analog to digital converter 9, the power management capabilities may not be necessary and may be excluded from the sensor device 2.

The sensor device 2 has a connector 14 that is configured to connect with the universal connection port 16 on the generic activator module 3. The connector 14 and the universal connection port 16 may be configured in any manner known in the art for performing the functions described herein. The purpose of the interface is to transfer power to the sensor device 2 and data to and from the sensor device 2. Examples of methods for transferring power though the interface 14, 16 are through galvanic connectors, through inductive or capacitive coupling. Examples of methods for transferring data through the interface 14, 16 are through galvanic connectors or using optical data transfer. In one embodiment, the connector 14 and the universal connection port 16 may each be a universal asynchronous receiver/transmitter (UART), and thus may include an integrated circuit to translate data between parallel and serial forms. The universal connection port 16 and the connection port 14 may alternatively be I$^2$C or Serial Peripheral Interface (SPI). The data communication between the sensor device 2 and the activator module 3 may alternatively be implemented using RF communication such as Bluetooth, near field communication (NFC), ANT or any other protocol suitable for short range communication. Due to the close proximity of the sensor device 2 and the activator module 3, the RF power required and the antennae can be optimized to provide very local RF communication.

In any embodiment, the universal connection port 16 is configured to receive and connect with the connectors 14 of various types of sensor devices 2. For example, the connector 14 may be configured identically for all types of sensor devices 2. In other embodiments, the connector 14 may be configured differently for various types of sensor devices 2. For example, the connector may have more or less connection points for transmitting digitized physiological data and power depending on the type of sensor device 2 and how many data channels are collected. The connection points may be electrical contact points, aligned inductive coils, aligned optical components, or any connects capable of transferring data and power between the generic activator module 3 and a sensor device. As another example, the connector 14 may provide a connection point to an identification chip or element 13 in a sensor device 2 to provide an identification pin for the sensor device 2 to the generic activator module 3. Alternatively, in other sensor devices 2 an identification pin for the sensor device 2 to the generic activator module 3 may be provided by a processor 10. The universal connection port 16 may be configured to connect with each such connector of various sensor devices.

When the connector 14 of the sensor device 2 is connected the generic activator module 3, power is provided from the generic activator module 3 to the sensor device 2, and digital physiological data is provided from the sensor device 2 to the generic activator module 3. Additionally, the sensor device 2 may identify itself to the generic activator module 3 through the connector 14 in communication with the universal connection port 16. A sensor device 2 may have an identification chip or element 13 which provides an identification pin for that sensor device 2. In the embodiment of FIG. 1, the identification device 13 of the sensor device 2 is in communication with the identification receiver 18 of the generic activator module 3. The identification receiver 18 then communicates the identification pin to the processor 26 of the generic activator module 3 such that the generic activator module 3 can identify the sensor device 2 to which it is connected. In another embodiment, the processor 10 of the sensor device 2 may directly provide an identification pin through the connector 14 and the universal port 16 to the processor 26 of the generic activator module 3. In such an embodiment, a sensor device 2 may not contain any identification device 13. However, in embodiments where the sensor device 2 does not have a processor or where the processor of a sensor device 2 does not provide an identification pin, the identification device 13 may be employed.

In the embodiment of FIG. 1, the generic activator module 3 has a processor 26 that receives digital physiological data transmitted from the sensor device 2. The processor 26 may be configured to process the digital physiological data prior to transmitting the data to the host device 4 or displaying the physiological data on the user interface display 24. In other embodiments, the processor 26 of the generic activator module 3 may not process the digital physiological data at all, as generic activator module 3 may receive digital physiological data from a sensor device 2 and relay that data to a host device 4 via a wireless connection to the host device. As described with respect to exemplary embodiments herein, the processor 26 may be configured to detect the type of sensor device 2 to which the generic activator module 3 is connected and to conduct various levels of data processing depending on the configuration of the generic activator module 3 and depending on the sensor device 2 to which the generic activator module 3 happens to be connected.

The processor 26 may also control the user interface display 24 to display physiological information about the patient. The displayed physiological information may be calculated by the processor 26 based on the digital physiological data received from the sensor device 2 or by the processor 10 in the sensor device. For example, if the sensor device 2 is an ECG sensor device 42 (FIG. 3), the processor 26 may process digital ECG data received from the ECG sensor device to calculate a heart rate, and then may display the heart rate on the user interface display 24. In an alternative embodiment, the ECG sensor device 42 may contain a processor 10 that calculates the heart rate on the digital ECG data. In such an embodiment, the processor 26 of the generic activator module may simply operate to display the heart rate calculated at the ECG sensor device 42 on the UI display 24.

The processor 26 may operate radio frequency antenna/transmitter 28 to transmit data to a host device 4, where the data may be further processed and/or stored. The radio frequency antenna/transmitter 28 of the generic activator module 3 and the RF antenna/transmitter 30 of the host device 4 may be any devices known in the art for wirelessly transmitting data between two points. In one embodiment, the RF antenna/transmitters 28 and 30 may be body area network (BAN) devices, such as medical body area network (MBAN) devices, that operate as a wireless network of wearable or portable computing devices. In such an embodiment, one or more generic activator modules 3 which may be connected to various sensor devices 2 attached to the patient may be in communication with a host device 4 positioned in proximity of the patient. Other examples of radio protocols that could be used for this purpose are Bluetooth, Bluetooth Low Energy (BLE), ANT and ZigBee.

Figure 3:
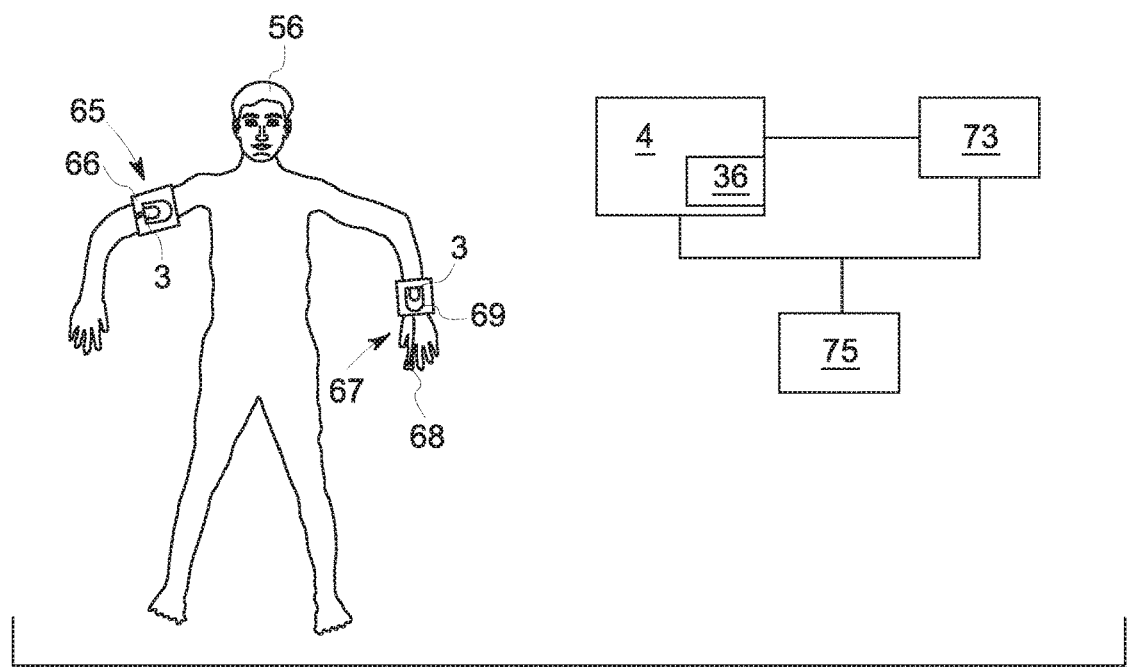
FIG. 3 depicts another embodiment of a wireless patient monitoring system configured to monitor a patient.

For example, turning to FIG. 3, a patient 56 may be monitored by two or more sensor devices 2, such as a noninvasive blood pressure sensor device 65 and a pulse oximeter sensor device 67. Each of the sensor devices 65 and 67 may be engaged with a generic activator module 3 to activate and power the sensor devices 65 and 67 and transmit the data collected by each of the sensor devices 65 and 67 to a host device 4. In an embodiment where the host device 4 is a part of a BAN, the host device 4 would be in proximity to the patient 56, such as attached to the patient's body, placed on or near the patient's bed, or positioned within range of the patient such as in the same room as the patient.

Any host device 4 may have a user interface 36 which may display data from the various sensor devices 65 and 67 on the same BAN for the patient 56. The host device 4 may further transmit the physiological data for the patient gathered by the sensor devices 65 and 67 to a central monitoring station 73 and/or to a central storage location 75. The central monitoring station 73 may provide a central location for attending clinicians to monitor patient status and/or receive alarm notifications. The central monitoring station 73 may be a local network having servers housed within a medical facility, or it may be a cloud-based system hosted by a cloud computing provider. The central storage 75 may be a central storage location for patient information to be stored long term, such as information that may become part of a patient's medical record and/or may be accessible by a attending clinician from any remote location.

In another embodiment, the host device 4 may be a remote device, such as central hub for a network of many monitoring devices within a healthcare facility or a subset of a healthcare facility. In such an embodiment, the RF receiver/transmitter 28 of the generic activator module and the RF receiver/transmitter 30 of the host device may operate on a longer-range wireless network, such as a network operating on the wireless medical telemetry service (WMTS) spectrum or on a WiFi-compliant wireless local area network (WLAN). In such an embodiment, the host device 4 may be receiving digital physiological data from two or more generic activator modules 3 connected to different patients within range of the host device 4. For example, a host device may be associated with a section of a healthcare facility, such as a unit or a floor, and may receive digital physiological data from all of the patients in that area.

The processor 26 may be further configured to operate the power gauge and protection module 22 which is connected to the battery 20. Thereby, the processor 26 and the power gauge and protection module 22 may regulate the power distribution within the generic activator module 3 and the sensor device 2. For example, the power from the battery 20 may be distributed to power the processor 26, the UI display 24 and the RF antenna/transmitter 28 in the generic activator module. The battery 20 may be any battery capable of providing sufficient power, and is preferably a rechargeable battery. Further, when the generic activator module 3 is connected to a sensor device 2, power is further distributed from the battery 20 through the power gauge and protection module 22 to the sensor device 2 through the universal connection port 16 and the connector 14. As described above, the sensor device 2 may have a power supply module 12 that distributes power within the sensor device 2. Alternatively, the power gauge and protection module 22 may distribute power directly to devices within the sensor device 2, such as to the A/D converter 9, processor 10, and/or identification device 13.

The host device 4 has receiver/transmitter 30 which is in communication with the RF receiver/transmitter 28 and the generic activator module 3. The host device may further comprise a processor 32, a user interface 36, and digital storage 34. The processor 32 may further process digital physiological data received from one or more generic activator modules 3 in communication with the host device 4. The host device may further display the patient's physiological information on the user interface 36. The user interface 36 may be utilized by a clinician to view details of the digital physiological data collected by the sensor devices 2. The user interface 36 of the host device 4 may be used by a clinician to view aspects of the digital physiological data for the patient that are not viewable on the display of the generic activator module 3. For example, in an embodiment where a sensor device 2 is an ECG sensor device 42, a clinician may not be able to review ECG waveforms recorded by the ECG sensor device 42 on the user interface 36 of the host device 4 because, in some embodiments, the user interface display 24 of the generic activator module 3 may be too small to display full waveforms, such as ECG waveforms.

The host device 4 may also have a digital storage device 34 for storing the physiological data collected by the various sensor devices 2 in communication with the host device 4 through various generic activator modules 3. The storage location 34 may also store processed physiological data created by the processor 32 of the host device, the processor 26 of the generic activator module 3, and/or the processor 10 of the sensor device 2.

The sensor devices 2 may be attached to the patient by various mechanisms so that the wireless patient monitoring devices can be worn, or maintained, on or near the patient and the patient can remain mobile and not get tangled, disconnected, or loosing monitoring. For example, as shown in FIG. 3, the noninvasive blood pressure sensor device 65 may be attached to the blood pressure cuff 66 which may be worn by the patient. Likewise, the pulse oximeter sensor device 67 may be attached to wristband 69 which may be worn by the patient. In other embodiments, various sensor devices 2 may be attached to the patient by various means which are proximate to the area where the patient detectors 8 are attached to the patient. For example, an ECG sensor device 42 (FIG. 4) may be connected to the patient via a chest strap or a waist strap. In another embodiment, an EEG sensor device may be attached to a patient by a headband, neckband, chest band, or armband, or may be attached directly to an ECG electrode or a separate accessory adhered to the skin of the patient. The generic activator module 3 would then connect to and be worn with each sensor device 2 wherever that sensor device is contained on the patient.

Figure 4:
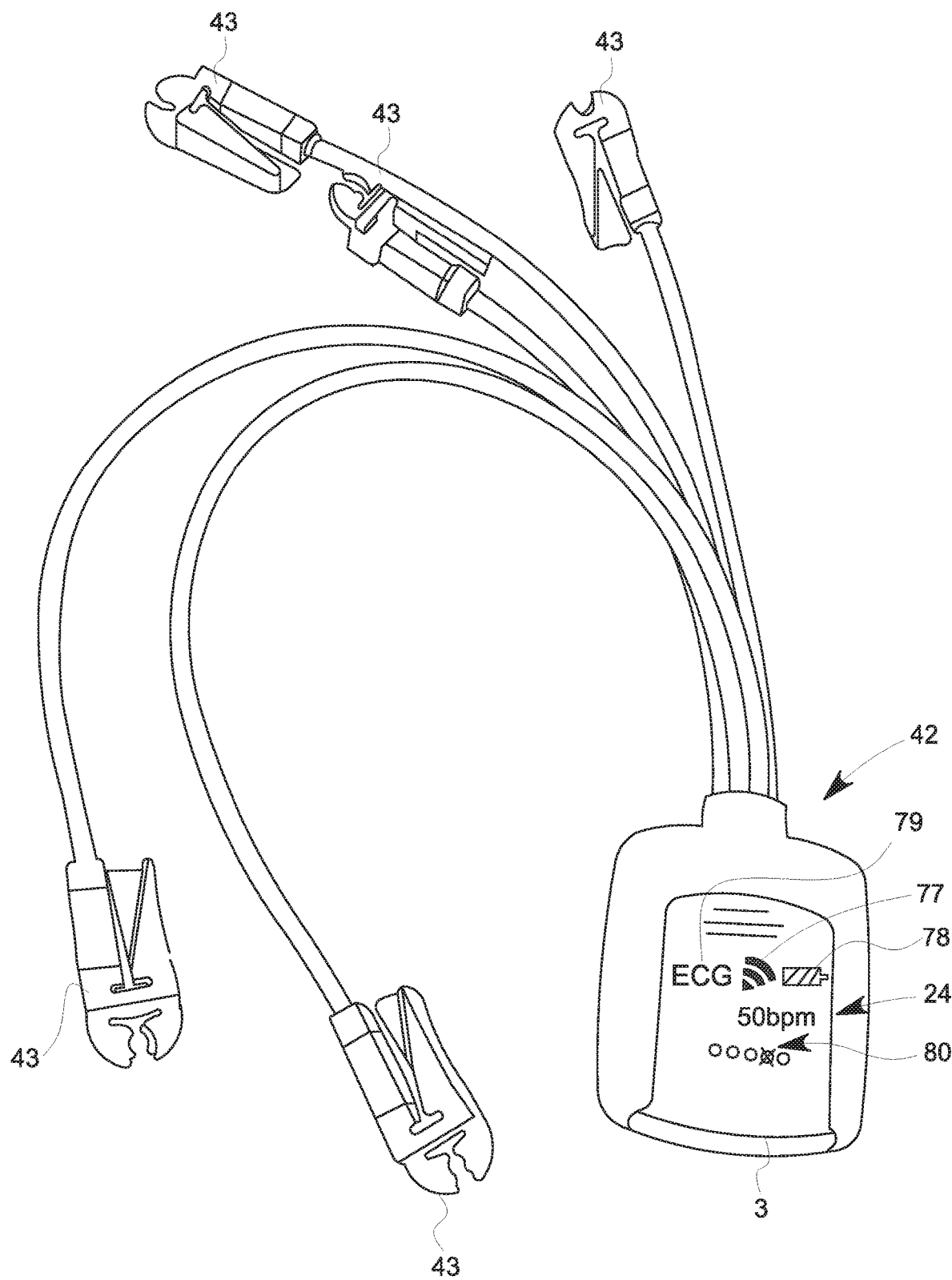
FIG. 4 depicts another embodiment of a wireless monitor including an ECG sensor device and a generic activator module.

Exemplary displays 24 for generic activator modules 3 are provided in FIGS. 4-7. FIG. 4 depicts an ECG sensor device 42 connected to a generic activator module 3. The ECG sensor device 42 has ECG detectors 43 that collect ECG data from a patient. It should be understood that the ECG detectors 42 may be any sensors, leads, or other devices capable of detecting patient cardiac signals. In the embodiment of FIG. 4, the display 24 of the generic activator module 3 displays the letters "ECG" on the connected device indicator 79 to signify that the generic activator module 3 is connected to an ECG sensor device 42.

The display 24 in FIG. 4 also displays a heart rate in beats per minute (BPM), which may be calculated by a processor in the generic activator module 3 or in the sensor device 2 based on the physiological data collected by the detectors 43. The display 24 may also provide a wireless connection status indicator 77 to indicate the status of the connection between the generic activator module 3 and the host device 4. The wireless connection status indicator 77 in FIG. 4 is a series arched lines that light up to show the wireless connection strength between the generic activator module 3 and the host device 4. However, the wireless connection status indicator 77 may take on any form capable of communicating the connectivity strength or status between the RF receiver/transmitter 28 of the generic activator module 3 and the RF receiver/transmitter 30 of the host device 4. For example, the wireless connection status indicator 77 may simply indicate the presence or absence of a wireless connection between the generic activator module 3 and the host device 4. The display 24 may also have a charge status indicator 78 to indicate the charge level of the battery in the generic activator module 3. The display 24 may also have an indicator to indicate the pairing status of the sensor (not shown), i.e. if the sensor is currently paired to a host device.

Additionally, the display unit may contain a detector status indicator 80 to indicate the status of the detectors 43 and their connectivity to the patient. In the embodiment shown in FIG. 4, the detector status indicator 80 is a series of five dots, each representing one of the detectors 43. The fourth dot is provided with an "x" through it to indicate that the sensor associated with that dot is not properly connected to the patient. This may be because the lead and/or the sensor are not properly connected to the patient, or it may be due to a failure of the detector device. In other embodiments, the detector status indicator 80 may be provided in any manner that would effectively communicate whether the detectors 43 are properly functioning and detecting physiological information from the patient. For example, the display 24 may provide a "sensor off" notification if a detector 43 is not properly connected to a patient, or it may provide a "sensor failure" notification if a detector 43 is not functioning properly.

The display 24 may also provide various other indicators. In other embodiments, the display 24 may offer a system function indicator to indicate whether the sensor device 2 and/or the generic activator module 3 are functioning properly and, if a malfunction occurs, indicate what the malfunction or problem is.

Figure 5:
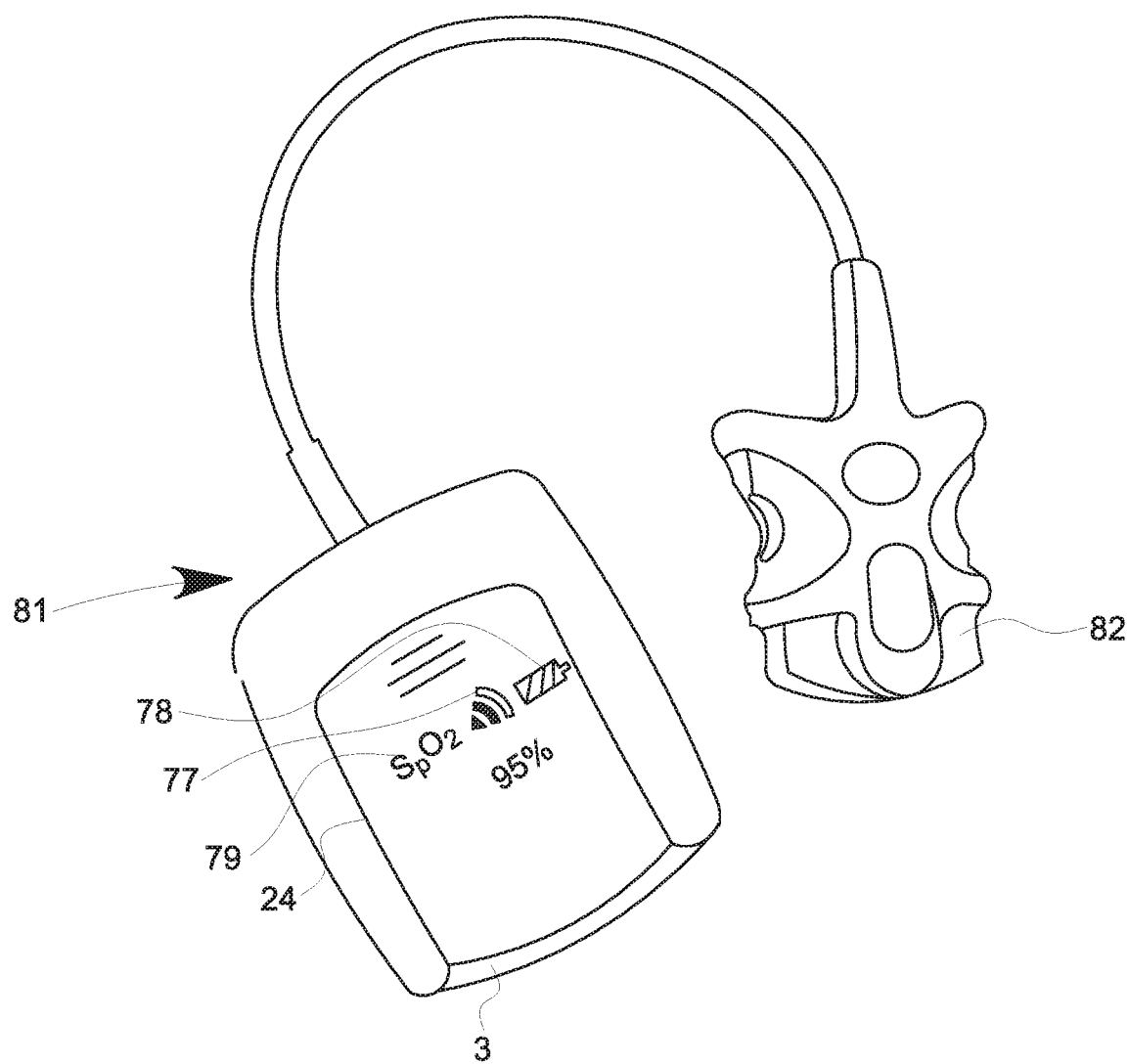
FIG. 5 depicts another embodiment of a wireless monitor including a pulse oximeter sensor device and a generic activator module.

FIG. 5 depicts a pulse oximeter sensor device 81 connected to a generic activator module 3. The pulse oximeter sensor device 81 has a pulse oximeter detector 82 that attaches to a patient, such as the patient's finger or ear, to measure blood oxygenation. In the embodiment of FIG. 5, the display 24 of the generic activator module 3 provides a connected device indicator 79 displaying "SpO$_2$" and an SpO$_2$ percentage value calculated based on the measurements taken by the pulse oximeter detector 82 connected to a patient.

Figure 6:
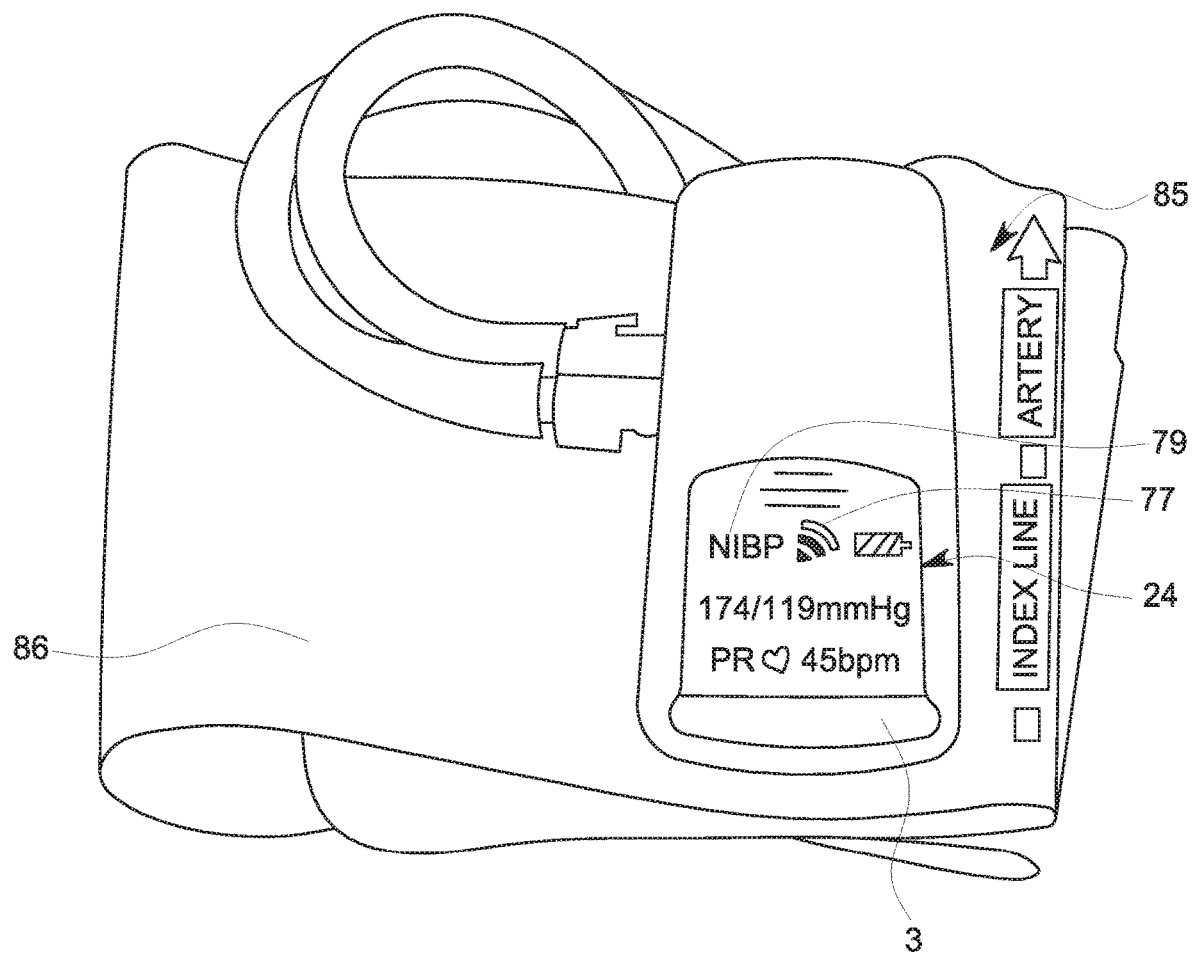
FIG. 6 depicts another embodiment of a wireless monitor including a blood pressure sensor device and a generic activator module.

FIG. 6 provides an example embodiment of a noninvasive blood pressure (NIBP) sensor device 85 paired with a generic activator module 3. The NIBP sensor device 85 has a blood pressure cuff 86 to noninvasively measure a patient's blood pressure. The information gathered by the noninvasive blood pressure cuff 86 is communicated from the NIBP sensor device 85 to the generic activator module 3 as described above. The display 24 of the generic activator module 3 provides a connected device indicator 79 displaying "NIBP" to indicate that the generic activator module 3 is paired with an NIBP sensor device 85. The display 24 also displays the blood pressure value for the patient as well as the patient's pulse rate, which are values calculated based on the blood pressure data measured by the blood pressure cuff 86.

Figure 7:
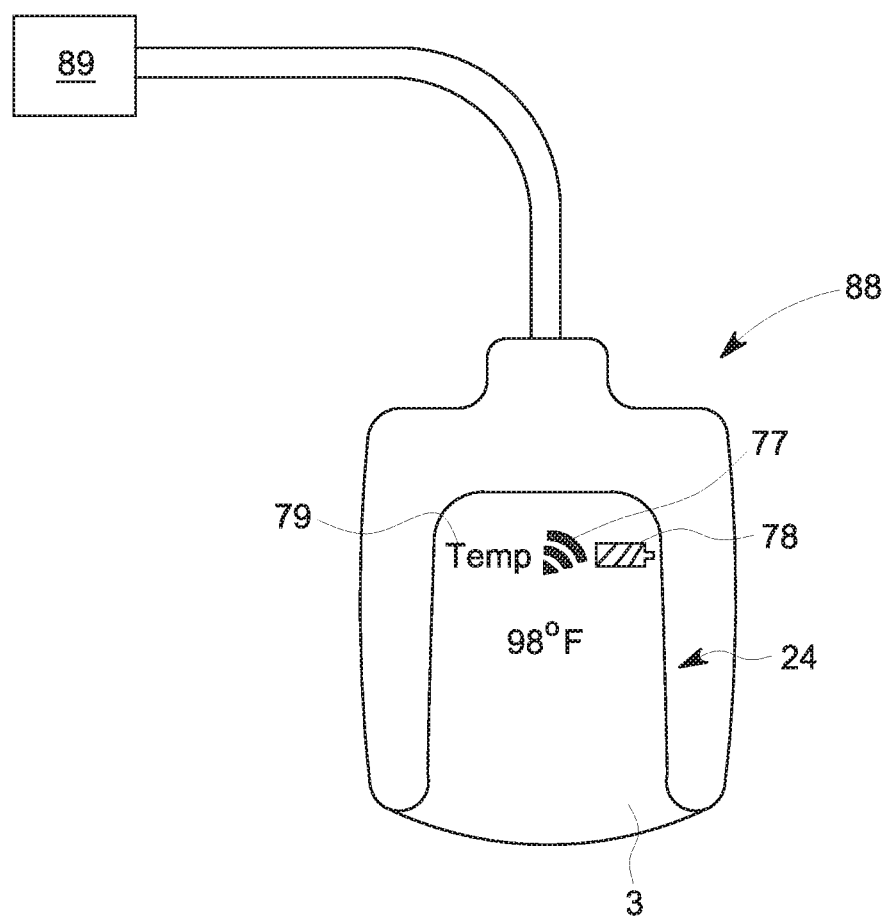
FIG. 7 depicts another embodiment of a wireless monitor including a temperature sensor device and a generic activator module.

FIG. 7 depicts an embodiment of a temperature sensor device 88 connected to a generic activator module 3. The temperature sensor device 88 has a temperature detector 89 which is attachable to a patient to measure the patient's temperature. The temperature detector 89 may be, for example, an adhesive thermometer device that adheres to a patient, such as on a patient's forehead, neck, or armpit, to measure the temperature of that location on the patient or a central temperature sensor, such as a catheter. The display 24 of the generic activator module 3 has a connected device indicator 79 displaying "temp" to indicate that the generic activator module 3 is paired with a temperature sensor device 88. Further, the display 24 of FIG. 7 is displaying a temperature measured by the temperature sensor device, which is displayed as 98° F. Likewise, the wireless connection status indicator indicates the wireless connection status of the generic activator module 3 and the charge status indicator 78 indicates the battery charge of the generic activator module 3.

Each type of sensor device 2, such as those described herein, may have varying levels of complexity. For example, the ECG sensor device 42 of FIG. 4 may contain a processor to process the ECG data collected by the detectors 43 to determine or calculate information based on the measured cardiac signals, such as heart rate and/or the presence of abnormal waveforms. In other embodiments, the ECG sensor device 42 may not contain any processor 10 and the digitized raw physiological data may be sent from the ECG sensor device 42 to the generic activator module 3 there to bear with. In such an embodiment, the generic activator module 3 may contain a processor that processes the digitized raw ECG data detected by the ECG sensor device 42. In still other embodiments, the generic activator module 3 may not process the digitized raw ECG data and may simply relay the data to the host device 4 via the RF receiver/transmitter 28 housed therein.

Certain sensor devices may be larger and more complicated and thus may necessitate having an internal processor 10 and/or an internal power supply 12 housed therein. For example, an NIBP sensor device 85 requires more significant electromechanical elements to operate the blood pressure cuff which may require power management to be internal to the NIBP sensor device 85. Thus, it may be preferable to house a processer 10 within the NIBP sensor device 85 which can process the physiological data gathered by the blood pressure cuff 86. Conversely, the temperature sensor device 88 may be a very simple device, and it may be preferable to not include a processor or power management within the temperature sensor device 88. In one embodiment, the temperature sensor device 88 may be a disposable device, and thus for cost reasons, it would be preferable to limit the amount of elements in the temperature sensor device 88 to limit the cost of the disposable device.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A wireless patient monitor comprising:
an activator module having:
an activator module housing;
a battery contained in the activator module housing;
a radio transmitter contained in the activator module housing configured to wirelessly communicate to a host device;
a universal connection port on the activator module housing configured to provide power from the battery to only one paired sensor device at any given time and to receive digital physiological data from the one paired sensor device;
at least two different sensor devices, each configured to monitor a different physiological parameter from the other;
wherein each of the at least two different sensor devices is configured to pair with the activator module, one at a time, each having a sensor device housing shaped to pair with the activator module housing such that the universal connection port contacts a connector on the sensor device housing of the one paired sensor device of the at least two different sensor devices to provide power from the battery to the one paired sensor device of the at least two different sensor devices and receive digital physiological data from the one paired sensor device.

2. The wireless patient monitor of claim 1, wherein the sensor device housings of each of the at least two different sensor devices is shaped to slidably connect with the activator module housing.

3. The wireless patient monitor of claim 2, wherein the sensor device housing of each of the at least two different sensor devices has a connection portion having a front face, wherein the connector is on the front face; and
wherein the activator module housing has a back face, wherein the universal connection port is on the back face of the activator module housing;
wherein the front face of the sensor device housing is configured to slide with respect to the back face of the activator module housing.

4. The wireless patient monitor of claim 2, wherein the universal connection port is configured to contact the connector on the sensor device housing of the one paired sensor device when the activator module housing is fully slidably connected to the sensor device housing.

5. The wireless patient monitor of claim 1, wherein the sensor device housing of each of the at least two different sensor devices is shaped to receive the activator module housing thereon.

6. The wireless patient monitor of claim 5, wherein the activator module housing is configured to be inserted into a connection portion of each of the at least two different sensor devices.

7. The wireless patient monitor of claim 1, wherein the sensor device housings of each of the at least two different sensor devices includes a connection portion configured to slidably connect with the activator module housing.

8. The wireless patient monitor of claim 1, further comprising a second activator module that is identical to and interchangeable with the activator module so as to interchangeably provide power from the battery to either one of the at least two difference sensor devices and receive and wirelessly transmit digital physiological data from either one of the at least two difference sensor devices.

9. The wireless patient monitor of claim 1, wherein the least two different sensor devices includes any two of a pulse oximeter sensor device, a temperature sensor device, a blood pressure sensor device, an electrocardiograph (ECG) sensor device, and an electroencephalograph (EEG) sensor device.

10. A wireless patient monitor comprising:
a first activator module having:
a first activator module housing;
a battery contained in the first activator module housing;
a radio transmitter contained in the first activator module housing that wirelessly communicates to a host device;
a universal connection port on the first activator module housing configured to provide power from the battery to only one paired sensor device at any given time and to receive digital physiological data from the one paired sensor device;
a first sensor device configured to be paired with the first activator module, wherein the first sensor device receives a first physiological information from at least one patient sensor, the first sensor device comprising:
a first sensor device housing;
a first analog-to-digital converter in the first sensor device housing to convert the first physiological information to a first digital physiological data;
a first connector on the first sensor device housing configured to transmit the first digital physiological data and to receive power to power the first sensor device;
a second sensor device configured to be paired with the first activator module, wherein the second sensor device receives a second physiological information from at least one patient sensor and wherein the second physiological information describes a different physiological parameter than the first physiological information, the second sensor device comprising:
a second sensor device housing;
a second analog-to-digital converter in the second sensor device housing to convert the second physiological information to a second digital physiological data;
a second connector on the second sensor device housing configured to transmit the second digital physiological data and to receive power to power the second sensor device;
wherein the first sensor device housing and the second sensor device housing are each shaped to pair with the first activator module housing such that the universal connection port contacts the paired one of the first connector on the first sensor device housing and the second connector on the second sensor device housing to provide power from the battery to the paired sensor device and receive digital physiological data from the paired sensor device.

11. The wireless patient monitor of claim 10, wherein the sensor device housings of each of the first sensor device and the second sensor device is shaped to slidably connect with the activator module housing.

12. The wireless patient monitor of claim 11, wherein each of the first sensor device housing and the second sensor device housing has a connection portion having a front face, wherein the first connector is on the front face of the first sensor device housing and the second connector is on the front face of the second sensor device housing; and
wherein the activator module housing has a back face, wherein the universal connection port is on the back face of the activator module housing;

wherein the front face of the first sensor device housing and the second sensor device housing is configured to slide with respect to the back face of the activator module housing.

13. The wireless patient monitor of claim 11, wherein the universal connection port is configured to contact the first connector or the second connector when the activator module housing is fully slidably connected to the first sensor device housing or the second sensor device housing.

14. The wireless patient monitor of claim 10, wherein the first sensor device housing and the second sensor device housing are each shaped to receive the activator module housing.

15. The wireless patient monitor of claim 14, wherein the activator module housing is configured to be inserted into a connection portion of the first sensor device housing and the second sensor device housing.

16. The wireless patient monitor of claim 10, wherein each of the first sensor device housing and the second sensor device housing includes a connection portion configured to slidably connect with the activator module housing.

17. The wireless patient monitor of claim 10, wherein the first sensor device and the second sensor device comprise any two of a pulse oximeter sensor device, a temperature sensor device, a blood pressure sensor device, an electrocardiograph (ECG) sensor device, and an electroencephalograph (EEG) sensor device.

18. The wireless patient monitor of claim 17, wherein the first connector is different than the second connector.

19. The wireless patient monitor of claim 10, further comprising a second activator module that is identical to the first activator module, wherein each of the first activator module and the second activator module interchangeably connect with the first sensor device and the second sensor device to provide power from the battery to the respective sensor device and receive and wirelessly transmit digital physiological data from the respective sensor device.

* * * * *